(12) United States Patent
Kunze et al.

(10) Patent No.: US 8,841,341 B2
(45) Date of Patent: Sep. 23, 2014

(54) PHARMACEUTICAL COMPOSITION EFFECTIVE AGAINST BIOFILMS

(75) Inventors: Brigitte Kunze, Braunschweig (DE); Irene Wagner-Döbler, Evessen (DE); Herbert Irschik, Wolfenbuttel (DE); Heinrich Steinmetz, Hildesheim (DE); Dietmar Schummer, Langen (DE)

(73) Assignee: Helmholtz-Zentrum fuer Infektionsforschung GmbH, Braunschweig (DE)

( * ) Notice: Subject to any disclaimer, the term of this patent is extended or adjusted under 35 U.S.C. 154(b) by 698 days.

(21) Appl. No.: 12/675,561

(22) PCT Filed: Sep. 5, 2008

(86) PCT No.: PCT/EP2008/061832
§ 371 (c)(1),
(2), (4) Date: Oct. 25, 2010

(87) PCT Pub. No.: WO2009/030773
PCT Pub. Date: Mar. 12, 2009

(65) Prior Publication Data
US 2011/0034708 A1      Feb. 10, 2011

(30) Foreign Application Priority Data
Sep. 5, 2007   (EP) .................................... 07115738

(51) Int. Cl.
*A61K 31/335*   (2006.01)
*A61K 8/02*   (2006.01)
*A61K 8/18*   (2006.01)
*A61K 31/365*   (2006.01)

(52) U.S. Cl.
CPC .................................. *A61K 31/365* (2013.01)
USPC .............................. 514/450; 424/401; 424/49

(58) Field of Classification Search
USPC ...................................... 514/450; 424/401, 49
See application file for complete search history.

(56) References Cited

U.S. PATENT DOCUMENTS
5,288,493 A * 2/1994 Martino et al. ............... 424/401

FOREIGN PATENT DOCUMENTS
WO       WO 02/099113       12/2002

* cited by examiner

*Primary Examiner* — Shengjun Wang
(74) *Attorney, Agent, or Firm* — Greer, Burns & Crain Ltd.

(57) ABSTRACT

The invention provides a compound termed Carolacton having the structure and derivatives thereof for medical use against biofilm formation by bacteria.

14 Claims, 1 Drawing Sheet

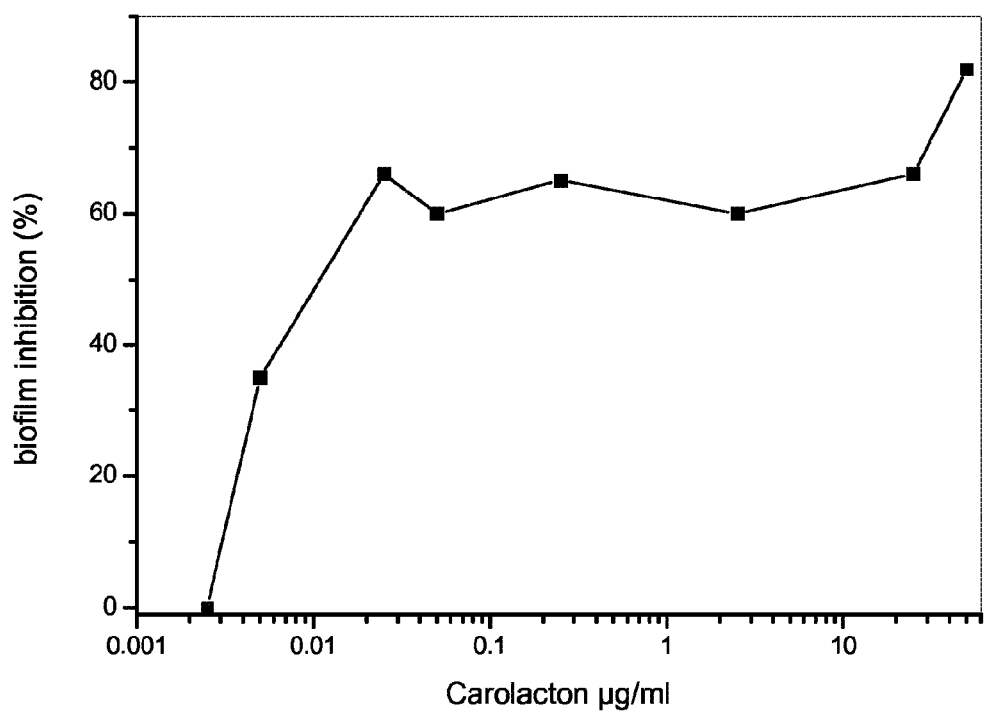

PHARMACEUTICAL COMPOSITION EFFECTIVE AGAINST BIOFILMS

The present invention relates to a pharmaceutical composition or medicament, which is effective against bio films formed by or comprising bacteria.

The present invention provides a pharmaceutical composition effective in the reduction or prevention of bacterial bio films, which bio films are generated on natural or synthetic surfaces in vitro or in vivo, e.g. on the surface of teeth in the form of dental plaque, or in infections which are chronic and persistent, e.g. cystic fibrosis associated pneumonia, or on implant surfaces, e.g. of the surface of stents, artificial joints, heartvalves or vessels.

STATE OF THE ART

Rasmussen et al. (Microbiology 152, 895-904 (2006)) give an overview of the mechanism leading to the formation of bacterial bio films, involving the coordinated gene expression in accordance with population density, which is termed quorum sensing. For gram-negative bacteria, quorum sensing has been identified to involve regulation by the secretion of diffusable signal molecules, e.g. acylhomoserine lactones (AHL) by the AHL synthase lux I homologue genes. Accumulation of the single molecules up to a certain threshold concentration leads to complexing with receptor proteins, e.g. the luxR gene product (Waters et al. (Annu Rev. Cell Dev. Biol 21, 319-346 (2005)), which AHL-receptor complex is a transcription activator for specific gene cassettes, e.g., for luciferase in *Vibrio fischeri*. In addition to the activation of transcription of a specific gene complex, transcription of the AHL synthase is activated, leading to a self-activating cycle. Rasmussen et al. describe specific competitive inhibitors for the acylated homoserine lactones as well as a screening assay to identify quorum sensing inhibitors using genetically modified bacteria.

Jefferson (FEMS Microbiology Letters 236, 163-173 (2004)) shows that at least in *Staphylococcus aureus* bio film formation, the production of exopoly saccharides is an important factor in the generation and structure of biofilms.

WO02/099113 A1 describes a compound with the basic structure of formula I of the present invention, and gives the biological activity as being antifungal only. Accordingly, there is mentioned the medical use of the compound as an antifungal agent.

Generally, in clinical infections involving bio film formation, an increased resistance of bacteria against antibiotics is found.

OBJECTS OF THE INVENTION

The present invention seeks to provide a compound having activity for the reduction or prevention of bio films, especially of bacterial bio films. Further, the present invention seeks to provide a pharmaceutical composition comprising the compound having activity against bio film formation by bacteria. Accordingly, the present invention seeks to provide the use of a compound for the production of a pharmaceutical composition for use against bio film formation, e.g. for use in the inhibition, reduction or prevention of biofilm formation by bacteria, including pathogenic bacteria.

GENERAL DESCRIPTION OF THE INVENTION

The invention achieves the above-mentioned objects by providing a compound comprising a structure according to formula I, its use for the production of pharmaceutical compositions, especially for medical use in the reduction, prevention and/or inhibition of biofilms. Firstly, the present invention provides a compound comprising a structure according to formula I, presently termed Carolacton, which is:

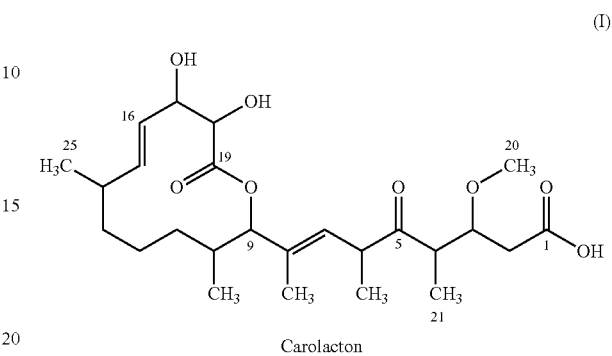

Carolacton

Further, the present invention provides derivatives of the compound according to formula I, wherein C-20, which is the carbon of the methyl group bound to C-3, is replaced by another carbon containing group R1, and wherein the acid group is esterified, i.e. hydrogen of the hydroxyl group of C-1 is substituted R2.

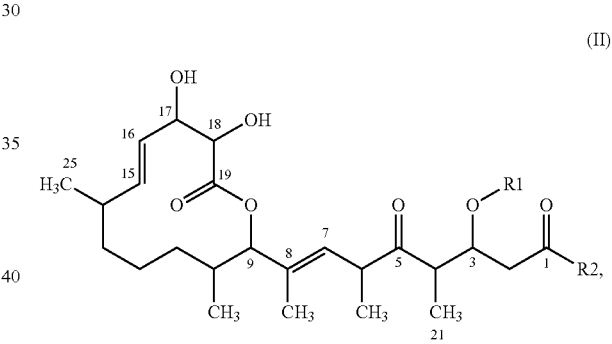

In (II), R1 and R2 are preferably independently chosen from hydroxy and $C_1$ to $C_{12}$ alkyl, alkylene, aryl, arylalkyl or aromatic groups, e.g. methyl, ethyl, n-propyl, isopropyl, n-butyl, isobutyl, n-heptyl, n-isoheptyl, n-pentyl- or isopentyl, n-hexyl, isohexyl or a $C_7$ to $C_{12}$ linear, branched or cyclic, saturated, unsaturated or aromatic hydrocarbon. For R1 being methyl and R2 being hydroxyl, compound II gives Carolacton of formula I. Accordingly, the invention also provides the use of compounds of formula II for the production of pharmaceutical compositions, especially for medical use in the reduction, prevention and/or inhibition of bio films, as well as medical compositions and pharmaceutical formulations containing a Carolacton of formula I or formula II for medical use in the reduction, prevention and/or inhibition of bacterial bio films. As a further derivative of Carolacton, the compound of formula II can carry an alkoxy group, especially a methoxy, ethoxy, or a $C_3$- to $C_{12}$-alkoxy group replacing the hydroxyl group linked to C-17 in formula I or II. Compounds, wherein the hydroxyl group of C-17 in formula I or II is replaced by a $C_1$- to $C_{12}$-alkoxy group, including alkoxy groups, wherein the alkyl is selected from the group consisting of n-propyl, isopropyl, n-butyl, isobutyl, n-heptyl, n-isoheptyl, n-pentyl- or isopentyl, n-hexyl, isohexyl or a $C_7$ to $C_{12}$ linear, branched or cyclic, saturated, unsaturated or aromatic hydrocarbon radicals, are also referred to as derivatives of Carolacton.

Further derivatives of the compounds according to formula I and formula II with for use in the production of pharmaceutical and/or cosmetic cosmetic compositions for use in the reduction, prevention and/or inhibition of bacterial biofilms have one or more of the following substitutions: As described for C-17, the hydroxyl group of C-18 can be replaced by an alkoxy group as described in relation to the hydroxyl group of C-17; the double bond connecting C-15 and C-16 and/or the double bond connecting C-7 and C-8 can each independently be hydrogenated to form saturated bonds, i.e. the double bonds can be replaced by single bonds, including formal saturation of the carbon atoms by additional hydrogen atoms; and/or the carbonyl group of C-5 can be converted to a hydroxy group.

Derivatives of Carolacton can be produced by total or partial chemical synthesis, and preferably by derivatization of Carolacton that is obtained by fermentation and isolation from the fermentation broth. Derivatization reactions for producing derivatives of the invention from Carolacton obtained by fermentation of a natural producer strain are known to the skilled person.

In summary, the following compounds are provided having activity against bacterial bio films, e.g. as components in pharmaceutical compositions for medical use and/or in cosmetic compositions:

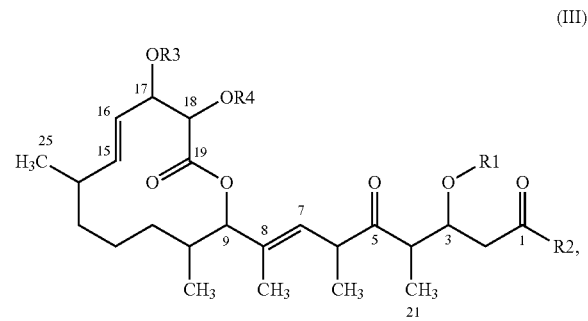

(III)

wherein each of R1, R2, R3 and R4 independently is selected from the group comprising or consisting of hydrogen and $C_1$- to $C_{12}$-alkyl groups, including methyl, ethyl, n-propyl, isopropyl, n-butyl, isobutyl, n-heptyl, n-isoheptyl, n-pentyl- or isopentyl, n-hexyl, isohexyl and $C_7$ to $C_{12}$ linear, branched or cyclic, saturated, unsaturated or aromatic hydrocarbon radicals,
wherein the bond connecting C-15 and C-16 is a double bond, or alternatively the bond is reduced to a single bond with C-15 and C-16 being saturated with hydrogen atoms,
wherein the bond connecting C-7 and C-8 is a double bond, or alternatively the bond is reduced to a single bond with C-7 and C-8 being saturated with hydrogen atoms, and
wherein C-5 carries a carbonyl group, or alternatively is reduced to a hydroxyl group.

Carolacton has no relevant antibiotic activity. Concentrations above 40 μg/mL are needed to inhibit *E. coli*. Against *E. coli* tolC, which has an impaired cell wall, an antibiotic activity at 60 ng/mL in vitro has been found.

Especially Carolacton as well as compounds comprising a structure according to formula II and III have been found to reduce or inhibit the formation of biofilms at very low concentrations, e.g. exemplified by *Streptococcus mutans*, a clinically important contributor to pathogenic bio films, e.g. in the generation of caries and endocarditis, preferably under anaerobic conditions like on surfaces of implants within the human or animal body. The inhibition of biofilm generation is achieved at concentrations as low as 0.005 μg/mL in in vitro cultures.

Compounds comprising a structure according to formulae II and III, exemplified by Carolacton of formula I, do not have a pronounced general antibiotic effect against bacteria. Therefore, a negative side effect from a general antibiotic activity of compositions comprising a compound according to formula II or III, e.g. of Carolacton, is essentially avoided.

Preferably, Carolacton or a compound according to formula II or according to formula III can be used as the active ingredient in pharmaceutical and in cosmetic compositions having an activity against bacterial bio film formation, the biofilms including or essentially consisting of Gram-negative and/or Gram-positive bacteria, e.g. the biofilm comprising *Streptococcus pneumoniae, Streptococcus pyogenes, Peptococcus/Peptostreptococcus* sp., *Staphylococcus aureus, Staphylococcus epidermidis, Burkholderia cepacia, Pseudomonas aeruginosa, Enterococcus faecalis, E. coli*, and clinical isolates of these, including pathogenic strains.

Further, the invention provides pharmaceutical composition, preferably further comprising non-toxic and pharmaceutically acceptable carrier, diluent, bulking and/or formulating agents, and at least one compound of the invention as the active ingredient. In accordance with the pharmaceutical activity of Carolacton and its derivatives, especially according to formulae I and II including derivatives according to formula III, the pharmaceutical composition of the invention is preferably provided for the reduction, prevention and/or inhibition of a bacterial biofilm, e.g. for the medical indication or medical diagnosis requiring the reduction, prevention and/or inhibition of a bacterial bio film, especially of an anaerobic bacterial biofilm. Accordingly, the pharmaceutical composition of the invention can be marked to be active or suitable for the reduction, prevention and/or inhibition of a bacterial bio film in medical indications requiring the reduction, prevention and/or inhibition of a bacterial biofilm. Further, the pharmaceutical composition of the invention can be marked to be active or suitable only for the reduction, prevention and/or inhibition of a bacterial bio film in medical indications requiring the reduction, prevention and/or inhibition of a bacterial bio film. Such medical indications include but are not limited to bacterial bio films on internal and external surfaces of hard and soft tissue, including mucosal surfaces, internal blood vessel surfaces, bone and cartilage surfaces, tooth surfaces, and the eye, especially in human beings, and bacterial bio films on implants of natural and/or synthetic materials, which implants can be arranged within a human body.

Further, the invention provides cosmetic compositions including at least one Carolacton compound, and the use of compositions containing at least one Carolacton compound for cosmetic purposes, e.g. a dental care formulation, compositions for use in the prevention or reduction of bacterial infections in the human eye, including contact lens care formulations. Further, the pharmaceutical compositions and the cosmetic compositions can be for use in indications requiring the reduction, prevention and/or inhibition of a bacterial bio film under essentially anaerobic conditions, and the compositions can be marked to be suitable for that use or indication, or marked to be suitable for that use or indication only.

BRIEF DESCRIPTION OF DRAWING

FIG. 1 shows a graphic representation of the biofilm inhibition in response to increasing concentration of carolacton under in vitro condition.

DETAILED DESCRIPTION OF THE INVENTION

The present invention is now described in greater detail with reference to the FIG. 1, showing a graphic representation of biofilm inhibition in response to increasing concentrations of Carolacton under in vitro conditions.

Example 1

Production of Compounds Comprising a Structure According to Formula I (Carolacton) and its Derivatives Compounds comprising a structure according to formula II can be produced from Carolacton according to formula I by derivatization, e.g. by transesterification to substitute R1 and/or R2 by different radicals, e.g. involving the use of standard synthesis methods, e.g. involving the binding and removal of protecting groups to atoms of formula I.

Carolacton can be produced by fermentation of myxobacteria, especially of *Sorangium cellulosum*, also called *Polyangium cellulosum*. For fermentation, strain DSM 19571, available from DSMZ GmbH, Braunschweig, Germany, was cultivated at 30° C. under aerobic conditions on agar plates containing casitone, Difco, 0.3%; $CaCl_2 \times 2H_2O$, 0.1%; yeast extract, Difco, 0.1%; agar 1.5% at pH 7.2, including a carbon source, e.g. glucose or starch at 0.1%. Alternatively, agar is used, containing 0.5% fresh baker's yeast and 0.1 calcium chloride at 1.5% agar, pH 7.2.

For fermentation, peptone from typically digested casein, 0.3%, calcium chloride at 0.05%, magnesium chloride at 0.2% and a carbon source, glucose or starch, at 0.1% can be used. Preferably, the following liquid medium is used for production of Carolacton: 0.8% starch, 0.2% yeast extract, 0.2% soy meal with fat removed, 0.1% calcium chloride, 1% magnesium chloride, 0.2% glucose, 8 mg/L NaFe(III)—EDTA, 1.19% HEPES-buffer, pH adjusted to 7.4 prior to autoclaving using 20% potassium hydroxide.

For the pre-culture, the preferred medium was used in 6 parallel 2-L-Erlenmeyer flasks containing 800 mL medium, inoculated with 60 mL culture each. The pre-culture was incubated on a rotary shaker at 160 rpm for three days at 30° C. For fermentation, the preferred medium was used, but omitting HEPES, maintaining the pH at or above 0.7 using 5% potassium hydroxide. To the medium, 1.5% (v/v) adsorber resin Amberlite XAD 16 (Rohm and Haas) was added. The stirrer speed was 100 rpm, aeration was at 1.0 v/v min. Carolacton production was measured using the antibacterial activity against *E. coli* tolC by extracting an aliquot from the fermenter after removal of XAD resin with methanol, and concentrating the methanol extract to 1/25 of the initial sample volume. Of the extract, 10 μL were applied to an antibiotic assay disc with 6 mm diameter and placed onto an agar plate inoculated with the test organism. After incubation for one day at 30° C., the inhibition zone was measured. Glucose was determined using the DIABUR—test 5000 test sticks available from Roche. The course of the fermentation is shown in table 1:

TABLE 1

| | | Course of fermentation | | |
|---|---|---|---|---|
| Time (days) | pH | $pO_2$ (%) | Glucose (%) | Inhibition zone diameter of *E. coli* tolC (mm) |
| 0 (start) | | | | |
| 3 | 7.06 | 85 | n.d. | n.d. |
| 4 | 7.07 | 50 | 0.3 | n.d. |
| 5 | 7.13 | 39 | 0.3 | 7 |
| 6 | 7.16 | 28 | 0.25 | 10 |
| 7 | 7.03. | 29 | 0.1 | 15 |
| 10 | 7.25 | 28 | 0 | 21 |
| 11 | 7.27 | 28 | 0 | 21 | n.d. = not determined

The fermentation was stopped on day 11. XAD was removed by sieving, Carolacton was produced to a final concentration of 3.4 mg/L broth.

From 100 L fermentation broth, the adsorber resin was harvested by filtration (210 μm pore size). The resin was washed with water for removal of adherent cells and extracted with 30% methanol in water. Elution was done with methanol (8 L) to yield raw Carolacton. After evaporation of the methanol, the residual water layer was extracted three times with ethyl acetate. The organic layer was dried with anhydrous sodium sulfate, filtrated, concentrated in vacuo, redissolved in methanol and extracted with n-hexane. After partition and removal of the hexane layer, methanol was evaporated to give a crude extract of 16.6 g.

For further purification, chromatography on a Sephadex LH20 (column 8×79 cm, eluent methanol, flow rate at 28 mL/min) was used. Thin layer chromatography and UV detection identified a spot containing a 8.2 g fraction of Carolacton, which was further separated on a Merck Prep bar 100 chromatography system (column 10×40 cm, 120Å 15 μm; solvent: methanol/ammonia acetate buffer at pH 5, 57:43, flow 17 mL/min, UV detection at 210 nm). After evaporation of the Carolacton containing fraction (1.3 g), preparative reverse phase chromatography is performed (column 3×48 cm: Kronlab ODS AQ 120Å 16 μL, solvent: acetonitrile/0.05 M ammonia acetate buffer adjusted to pH 5, 65:35, flow rate at 17 mL/min, UV detection at 206 nm) to yield 275 mg Carolacton after evaporation.

Carolacton of formula I could be characterized as follows: Formula $C_{25}H_{40}O_8$, MW=468.6, HRMS: [Cl$^-$] calculated: 468.2723. found: 468.2732, IR: ν [cm$^{-1}$] (1 gϵ)=204 (4.06), 259 (2.35), 290 (2.58); TLC (silica gel 254 nm): ethyl acetate/methanol/water 65/30/10, $R_f$=0.62; HPLC: solvent A (95/5 water/acetonitrile plus 5 mM $NH_4Ac$, pH 5.5), solvent B (5/95 water/acetonitrile plus 5 mM $NH_4Ac$, pH 5.5) gradient in 30 min from 10% B to 100% B, 10 min isocratic B, column 2×125 mm Nucleosil 120 5 μm C18 (Macherey Nagel), flow 0.3 mL/min, Rt=12.8 min.

For synthesis of derivatives of Carolacton compounds according to formula II and of formula III, the Carolacton obtained by fermentation was derivatized, e.g. by alkylating and hydrogenating reagents. Optionally, protective groups were introduced for regio-selective derivatization. Derivatives could be isolated from derivatization reaction compositions by standard procedures, preferably by HPLC.

$^1$H- and $^{13}$C-NMR data (600/150 MHz) of Carolacton (I) in dichloroform

| H | δ | m | J (Hz) | C | δ |
|---|---|---|---|---|---|
| 2 $H_b$ | 2.64 | dd | 15.5, 4.2 | 1 | 175.6 |
| 2 $H_a$ | 2.43 | dd | 15.7, 5.9 | 2 | 35.9 |
| 3 H | 3.73 | ddd | 8.5, 5.5, 4.5 | 3 | 80.1 |

-continued 1H- and 13C-NMR data (600/150 MHz) of Carolacton (I) in dichloroform

| H | δ | m | J (Hz) | C | δ |
|---|---|---|---|---|---|
| 4 H | 2.97 | dq | 8.3, 7.2 | 4 | 47.3 |
| 6 H | 3.48 | dq | 10.2, 6.8 | 5 | 213.3 |
| 7 H | 5.36 | d | 10.2 | 6 | 47.5 |
| 9 H | 4.74 | d | 11.3 | 7 | 129.4 |
| 10 H | 2.04 | m | — | 8 | 135.8 |
| 11 H$_b$ | 1.75 | m | — | 9 | 83.3 |
| 11 H$_a$ | 0.99 | m | — | 10 | 33.4 |
| 12 H$_b$ | 1.25 | m | — | 11 | 28.4 |
| 12 H$_a$ | 0.99 | m | — | 12 | 18.9 |
| 13 H$_b$ | 1.37 | m | — | 13 | 34.4 |
| 13 H$_a$ | 1.25 | m | — | 14 | 35.7 |
| 14 H | 2.31 | m | — | 15 | 134.5 |
| 15 H | 5.44 | ddd | 15.1, 9.8, 1.5 | 16 | 125.5 |
| 16 H | 5.52 | dd | 15.5, 2.3 | 17 | 73.0 |
| 17 H | 4.47 | s | br. | 18 | 73.7 |
| 18 H | 4.16 | d | 3.8 | 19 | 172.0 |
| 20 H$_3$ | 3.30 | s | — | 20 | 58.1 |
| 21 H$_3$ | 0.92 | d | 6.8 | 21 | 12.8 |
| 22 H$_3$ | 1.10 | d | 6.8 | 22 | 15.3* |
| 23 H$_3$ | 1.70 | s | — | 23 | 13.0 |
| 24 H$_3$ | 0.76 | d | 7.2 | 24 | 15.3* |
| 25 H$_3$ | 0.97 | d | 6.4 | 25 | 21.7 |

*interchangeable

Example 2

Inhibition of Bio Film Formation in In Vitro Culture

Using *Streptococcus mutans* as a model organism that generates biofilms, overnight cultures of *Streptococcus mutans* in THB medium (Todd Hewitt Broth, available from Bacto) were diluted 1:100 into fresh THB medium containing 0.5% wt/vol sucrose. For anaerobic growth, medium was flushed with nitrogen before use. Aliquots of the diluted culture (95 μL) of Example 1 were distributed into the wells of a 96-well polystyrene flat bottom microtiter plate, containing 5 μL of different concentrations of test compound or alternatively, 5 μL methanol as a control. Microtiter plates were incubated under aerobic and an anaerobic conditions, respectively, at 37° C. for approximately 24 hours. For non-biofilm forming growth, e.g. planktonic growth, cells were grown in THB without the additional sucrose under otherwise identical conditions.

Bacterial growth was monitored in the microtiter plate by optical density readings at 620 nm. Quantitative bio film formation was determined using the live/dead bacLight bacterial viability staining kit (available under catalogue number L13152 from Molecular Probes, Eugene, Oreg., USA). The kit incorporates two nucleic acid stains that differ in spectral characteristics and their ability to penetrate bacterial cell membranes. When used alone, the green fluorescing stain Cyto9 generally labels all bacteria in the population, whereas the red fluorescing stain propidium-iodide only penetrates bacteria having damaged membranes, causing a reduction in the Cyto9 stain fluorescence when both dyes are present.

For staining, the culture medium was removed from the microtiter plate wells and cells were washed once with 100 μL fresh THB medium to remove planktonic growing and loosely bound cells. According to all the manufacturer's instructions, the adherent bacteria, regarded as the bio film, were then stained for 15 min in the dark at room temperature, using 100 μL of a 1:1 mixture of the two dye components. Fluorescence was measured in a microtiter plate reader (Wallac Victor 1420 multilabel counter, PerkinElmer Life Sciences), equipped with detectors and filter sets for monitoring red and green fluorescence.

Quantitative bio film formation was calculated by dividing the fluorescence intensities of the stained biofilms for each well of the microtiter plate at an emission of 530 nm (green) by the fluorescence intensity at the emission of 630 nm (red). As 100% activity, the results obtained from wells only containing methanol as the control, instead of a test compound, was used. Under anaerobic conditions, Carolacton inhibited formation of biofilm from *Streptococcus mutans* at very low concentrations. Results are given in table 3 for Carolacton of formula I. Planktonic cultures were only slightly influenced at higher concentrations, as was determined by optical density readings.

TABLE 3

The inhibition of biofilm formation of *Streptococcus mutans* under anaerobic and aerobic conditions by Carolacton

| Carolacton concentration (μg/mL) | Biofilm inhibition (%) under aerobic conditions | Biofilm inhibition (%) under anaerobic conditions |
|---|---|---|
| 50 | 1 | 82 |
| 25 |  | 66 |
| 2.5 | 19 | 60 |
| 0.25 | 21 | 53; 77 (second experiment) |
| 0.05 |  | 60 |
| 0.025 | 21 | 66 |
| 0.005 |  | 35 |
| 0.0025 |  | −7 |

Results for anaerobic biofilm inhibition are also shown in the FIG. 1, giving a concentration dependent inhibition of biofilm formation in the form of a saturation curve for Carolacton concentrations up to 20 μg/mL.

For a determination of bio film inhibition in relation to the control, the activity value for the Carolacton comprising test well was subtracted from the value obtained for the control. At concentrations of 2.5 and 0.25 μg/mL Carolacton, respectively, bio film formation by *Streptococcus mutans* wild-type strain was inhibited by about 60% under anaerobic conditions.

When using quorum sensing negative mutants of *Streptococcus mutans*, which are defective in the quorum sensing pathway, the following results have been obtained the same testing conditions:

*Streptococcus mutans* com E (−) mutant: No significant inhibition; at a concentration of 2.5 μ/mL, Carolacton, 5% inhibition; at 0.25 μg/mL Carolacton, 12% inhibition. *Streptococcus mutans* com D (−) mutant: No significant inhibition, namely at both 2.5 μg and 0.25 μg/mL Carolacton, about 10% inhibition. *Streptococcus mutans* com C (−) mutant: Induction of biofilm formation between 150% (0.25 μg/mL Carolacton) and 200% (2.5 μg/mL Carolacton). *Streptococcus mutans* luxS mutant: Inhibition similar to wild-type (between 59% (2.5 μg/mL) and 46% (40.25 μg/mL), respectively).

At a concentration of 0.025 μg/mL Carolacton, biofilm formation under anaerobic conditions still was inhibited in vitro by about 65%.

In contrast to growth in bio films, planktonic growth was not influenced by Carolacton, or only marginally reduced. From the results with quorum sensing negative mutants, it can be inferred that Carolacton possibly interferes with signalling molecules or signal transduction of the quorum sensing systems.

It could be shown in these examples of *Streptococcus mutans* that Carolacton effectively inhibits formation of bacterial bio films especially under anaerobic conditions at low concentrations. Accordingly, a preferred use of the compounds of the invention is for the production of a pharmaceutical composition for medical or cosmetic use in conditions where anaerobic conditions dominate, e.g. in cosmetic and/or medical applications against dental plaque formation or in medical applications against biofilm generation within the human or animal body, e.g. on implant surfaces.

Similar results indicating activity against bacterial biofilm formation could be obtained for the Carolacton derivatives of formulae II and III.

The invention claimed is:

1. A method for reducing or inhibiting formation of a bacterial biofilm in a medical treatment, the method comprising selecting a natural or synthetic surface and providing to the surface a pharmaceutical composition comprising a compound having a structure according to formula (I)

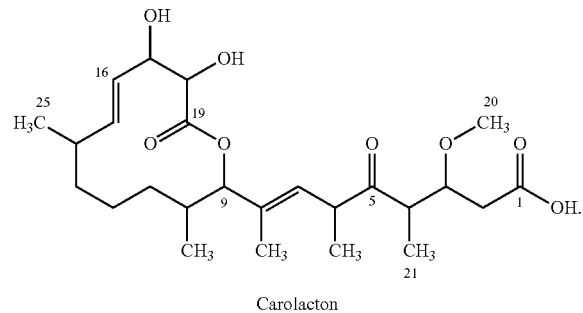

Carolacton

2. The method according to claim 1, wherein the bacterial biofilm comprises pathogenic bacteria.

3. The method according to claim 1, wherein biofilm formation is under essentially anaerobic conditions.

4. The method according to claim 3, wherein the anaerobic conditions are present on a surface of artificial implants or medical devices that are arranged within a human or animal body and wherein the pharmaceutical composition is applied to the surface of the artificial implants or medical devices.

5. The method according to claim 1, wherein the compound is produced by a process including a fermentation of *Sorangium cellulosum* and the isolation of Carolacton according to formula I from the fermentation broth.

6. The method according to claim 1, wherein the surface is selected from the group consisting of mucosa, teeth, the eye, bone tissue, cartilage tissue, an implant, and blood vessels.

7. The method of claim 1, wherein the medical treatment is a dental care treatment.

8. A method for reducing or inhibiting formation of a bacterial biofilm in a medical treatment, the method comprising selecting a natural or synthetic surface, providing to the surface a pharmaceutical composition comprising a compound having a structure according to formula I

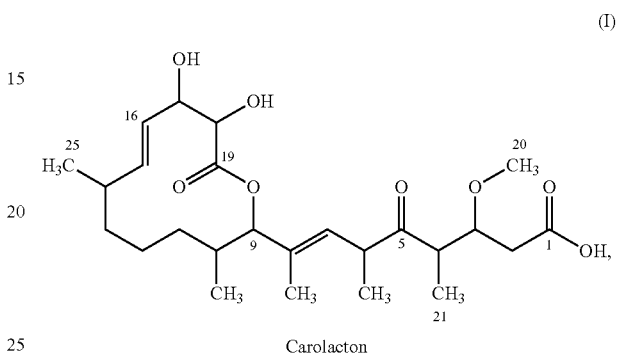

Carolacton wherein the hydrogen of the hydroxyl group of C1 is substituted with methyl.

9. The method according to claim 8, wherein the bacterial biofilm comprises pathogenic bacteria.

10. The method according to claim 8, wherein biofilm formation is under essentially anaerobic conditions.

11. The method according to claim 10, wherein the anaerobic conditions are present on a surface of artificial implants or medical devices that are arranged within a human or animal body and wherein the pharmaceutical composition is applied to the surface of the artificial implants or medical devices.

12. The method according to claim 8, wherein the compound is produced by a process including a fermentation of *Sorangium cellulosum* and the isolation of Carolacton according to formula I from the fermentation broth.

13. The method according to claim 8, wherein the surface is selected from the group consisting of mucosa, teeth, the eye, bone tissue, cartilage tissue, an implant, and blood vessels.

14. The method of claim 8, wherein the medical treatment is a dental care treatment.

* * * * *